United States Patent [19]

Daemer et al.

[11] Patent Number: 4,636,469
[45] Date of Patent: Jan. 13, 1987

[54] ISOLATION OF HEPATITIS A VIRUS STRAIN HM-175

[75] Inventors: Richard J. Daemer; Stephen M. Feinstone, both of Washington, D.C.; Ian D. Gust, Fairfield, Australia; Robert H. Purcell, Boyds, Md.

[73] Assignee: The United States of America as represented by the Secretary of the Department of Health & Human Services, Washington, D.C.

[21] Appl. No.: 686,524

[22] Filed: Dec. 26, 1984

Related U.S. Application Data

[63] Continuation of Ser. No. 366,165, Apr. 7, 1982, Pat. No. 4,532,215.

[51] Int. Cl.$^4$ .................. C12N 7/08; A61K 39/12
[52] U.S. Cl. .................................. 435/237; 424/89
[58] Field of Search .................... 424/89; 435/237

[56] References Cited

U.S. PATENT DOCUMENTS

| | | | |
|---|---|---|---|
| 3,838,004 | 9/1974 | Mebus et al. | 435/237 |
| 4,110,433 | 8/1978 | Purdy | 435/237 |
| 4,164,566 | 8/1979 | Provost et al. | 424/89 |

FOREIGN PATENT DOCUMENTS

EP8559  3/1980  European Pat. Off.
EP25745 3/1981  European Pat. Off.

OTHER PUBLICATIONS

Locarni et al, C.A. 94, #63153p (1981) of J. Virol., 1981, 37(1): 216-215.
Feinstone et al, C.A. 92, #54753r (1980) of Viral Hepatitis, Proc. Symp., 2nd (1978): 41-8.
Mathiesen et al, C.A., 88: 150297h (1978) of J. Clin. Microbiol., 1978, 7(2): 184-193.
Dienstag et al, C.A. 87: 132008q (1977) of Postgrad. Med. J., 1977, 53(621): 364-373.
Provost et al, C.A. 87: 66493r, 1977, of U.S. Pat. No. 4,031,203, Jun. 21, 1977.
Hilleman et al, C.A. 86: 195205b, 1977, of U.S. Pat. No. 4,017,601, Apr. 12, 1977.
Provost et al, C.A., 85: 121682n (1976) of German No. 2555169, 10 Jun. 1976.
Purcell et al, C.A., 84: 57267f (1976) of J. Immunol., 1976, 116(2) 349-356.
T. W. Fiennes, ed., Pathology of Simian Primates, Part II: Infectious and Parasitic Diseases, S. Karger, Basel (1972).
Daemer et al., Infection and Immunity, vol. 32, No. 1, Apr. 1981.
S.S.I.E. ZXE 247 6, Contract/Grant No.: Z01 AI 00026-13 LID, Purcell, R. H. et al, 10/76 to 9/80, Results: Progress: Hepatitis A virus has been isolated directly from the stool of a patient into primary African green monkey kidney cell culture.

Primary Examiner—Ronald W. Griffin
Attorney, Agent, or Firm—John S. Roberts, Jr.

[57] ABSTRACT

Human hepatitis A virus (HAV), taken directly from human clinical specimens, can be isolated and serially passaged in primary African green monkey kidney (AGMK) cell cultures. This strain induced antibody to HAV in inoculated chimpanzees and is useful for vaccine.

3 Claims, No Drawings

ISOLATION OF HEPATITIS A VIRUS STRAIN HM-175

This is a continuation of application Ser. No. 366,165, filed Apr. 7, 1982, now U.S. Pat. No. 4,532,215.

BACKGROUND OF THE INVENTION

Hepatitis A virus (HAV) has only recently been propagated in cell cultures and is very difficult to isolate. There are no more than six or eight strains yet isolated, and most of them require passage through another species or in cell lines that are not suitable for vaccine development. Since HAV cannot be produced in large quantities from tissure culture cells, the development of in vitro culture systems depended upon the development of the HAV-specific detection system by immunofluorescence (IF).

At the present time, marmosets are the major source for production of hepatitis A virus (HAV) and hepatitis A antigen (HA Ag). However, the decreasing availability of these animals and the high cost of acquiring and maintaining them necessitates an alternative source of antigen for serologic testing. This invention describes the HM-175 strain of HAV suitable for the production of tissue culture-grown HA Ag as an antigen for radioimmunoassay of anti-HAV.

The isolation of HAV directly from clinical specimens into a cell line for vaccine production (primary AGMK) suggests that additional in vitro cultivation of the virus will yield a strain suitable for vaccine development.

PRIOR ART STATEMENT

Provost et al, U.S. Pat. No. 4,164,566, teaches the development of in vitro Hepatitis A virus (HAV) cell cultures. Provost et al, however, uses a different strain of HAV which requires at least 5 passages in a subhuman primate in order to produce HAV. The purpose of this invention is to show that HAV can be isolated and serially passaged in primary African green monkey kidney (AGMK) cell cultures taken directly from human clinical specimens.

Daemer et al, *Infection and Immunity*, Vol. 32, No. 1, Apr. 1981, pp 388-393.

UTILITY STATEMENT

The growth of hepatitis A virus, strain HM-175 in primary African green monkey kidney provides a reliable and continuous source for the propagation of this virus and viral antigens. The antigen produced directly from this tissue culture provides material for vaccine production and for serologic testing.

DETAILED DESCRIPTION OF PROCESS

A new strain of HAV, HM-175, was isolated from clinical specimens derived from an outbreak of the virus in Australia. Stool suspensions were prepared either as 2% or 20% extracts in phosphate-buffered saline (PBS), pH 7.4, clarified by low speed centrifugation, and stored at $-70°$ C.

CELL CULTURES

Primary cell cultures of African Green Monkey kidneys (AGMK) were used for virus propagation. The maintenance medium was Eagle's minimal essential medium (MEM) with Earle's salts and 25 mM Hepes buffer. The medium was supplemented with 2% inactivated fetal bovine serum (FBS), 50 ug/ml of gentamicin, 2 u g/ml fungizone, and 2 mM glutamine. The cultures were then maintained in the medium at 37° C. for many weeks.

VIRUS PROPAGATION (a) Primary isolation

Cultures of AGMK cells were washed twice with Hanks balanced salt solution (HBSS) and inoculated with 0.1 ml of either a $10^{-1}$ or $10^{-2}$ dilution of stool material prepared as directed in the previous paragraph. The cells were allowed a 2-hour period of absorption, after which they were again sustained in maintenance medium and incubated at 37° C. The cultures were assayed by direct immunofluorescence for hepatitis A antigen (HA Ag) at weekly intervals.

(b) Serial passage

AGMK cells wee initially inoculated with 0.1 ml of a 1:20 dilution of stool containing HM-175 virus. For serial passage, the cells were harvested by treatment with trypsin-EDTA (ethylenediamintetraacetic acid), pelleted by low speed centrifugation and resuspended in 4 ml of maintenance medium.

(c) Immunofluorescence

Direct immunofluorescence was performed by staining with fluorescein-conjugated hyperimmune serum from a chimpanzee which had been infected with the MS-1 strain of HAV.

(d) Blocking tests

To confirm the specificity of the IF reactions, blocking tests were performed under code with paired sera from humans naturally infected with type A hepatitis and paired sera from a chimpanzee experimentally infected with the MS-1 strain of HAV. Blocking experiments were performed by preincubating the coverslips for 15 minutes with a 1:5 dilution of the serum to be tested. The slides were then stained with a 1:200 dilution of conjugated chimpanzee serum.

RESULTS

Table 1 lists attempts to isolate HAV in AGMK from clinical specimens that contained one of three different strains of HAV. Little or no antigen was detected in the cultures inoculated with MS-1 or SD-11. In the cell cultures inoculated with stool extract containing HM-175, HA Ag was observed in a small number of cells after seven days, both the number of cells and the intensity of staining increased with time. By 21 days post inoculation, scattered single fluorescing cells and foci of intensely fluorescing cells could be seen.

Cells inoculated with the 3-week or 8-week cell harvest of the first AGMK passage (HM-175 M-6, AGMK-1) were positive by IF for viral antigen by 2 weeks after inoculation (Table 2). The cells inoculated with the 3-week harvest remained positive by IF for at least 6 weeks, at which time the cells were harvested with trypsin-EDTA and used for a third cell passage. Whole cells were used because the viral antigen appeared to be cell associated, suggesting that cell-to-cell contact might facilitate infection of the cells. Weak but positive fluorescence was detected at 2 weeks after which no fluorescence was observed (fluorescence was subsequently detected at 11 weeks in the AGMK-3 culture maintained for that period of time). The cells were blind-passed (AGMK-4) at week 6, showing positive by 3-weeks postinoculation. By pass 5, fluorescence was detected at 1 week; by 3 weeks the intensity of staining and number of cells fluorescing had increased to greater than 75%. In the 6th passage, the cells were positive after 1 week and after 3 weeks, almost all cells were stained. Pass 7 cells were positive at 1 week and, by 5 weeks, most cells were positive.

TABLE 1

HAV IN AGMK CELL CULTURE: Primary Isolation

| Strain | Inoculum | IF by Week[a] | | |
|---|---|---|---|---|
| | | 1 | 2 | 3 |
| MS-1 | Stool | — | — | — |
| MS-1 | Serum | — | — | — |
| SD-11 | Stool | ± | —[b] | ± |
| SD-11 | Serum | — | 1 | 2 |
| HM-175 | Stool | 1 | 1 | 3 |

[a] Fluorescein-labeled anti-HAV was applied to acetone-fixed cell culture coverslips. The amount of HA Ag was determined on a scale of 1 to 4. 4 indicates that the cell sheet contained almost 100% intensely staining cells.
[b] $10^{-1}$ dilution of inoculum; nonspecific cell deterioration evident with $10^{-2}$ dilution.

TABLE 2

HAV IN AGMK CELL CULTURE - Cell Culture Passage (HM 175)

| Marmoset Passage | AGMK Passage | IF by Week | | | | | | |
|---|---|---|---|---|---|---|---|---|
| | | 1 | 2 | 3 | 4 | 6 | 8 | 11 |
| 0 | 1 | 1 | —* | + | 1 | 1 | 2 | 4 |
| | 2 | | | | | | 4* | |
| | 3 | — | ± | 3 | 4* | | | |
| | 4 | 2 | 2 | 4 | 4* | | | |
| | 5 | 1 | 2 | 3 | 4* | | | |
| | 6 | 1 | 1 | 3* | | | | |
| | 7 | 1 | 2 | 2 | 2* | | | |
| 6 | 1 | 2 | 3 | 4* | | | (RIA+)* | |
| | 2 (3)** | — | 4 | 4 | 1* | | | |
| | (8) | 1 | 1 | 4 | 4 | 4* | | |
| | 3 (3) | — | 1 | — | — | —* | — | 4 |
| | (8) | 1 | 1 | 1 | 1 | ±* | — | 4 |
| | 4 (3) | — | — | 1 | 2 | 2* | | |
| | (8) | — | — | 1 | 2 | 2* | | |
| | 5 (3) | 2 | 3 | 3 | 4* | | | |
| | (8) | 2 | 2 | 3 | 4* | | | |
| | 6 (3) | 1 | 2 | 3* | | | | |
| | (8) | 1 | 2 | 3* | | | | |
| | 7 (3) | 2 | 2 | 2 | 2 | | | |
| | (8) | ± | 1 | 3 | 3 | | | |

*Used for passage
**The second passage was made from a 3-week harvest and an 8-week harvest. These were then maintained and passaged separately.

In the case of the cells inoculated with the AGMK-1, 8-week harvest, granular cytoplasmic fluorescence was observed by one week after inoculation, although only approximately 1% of the cells were positively stained at that time. By 4 weeks, the number of positive cells had increased substantially to 80–90%. Cells were harvested at 6 weeks by treatment with trypsin-EDTA and used for a third passage in cell culture. As with the 3-week harvest above, whole cells were used. Radioimmunoassay (RIA) of this cell harvest yielded a P/N of 8.4. Weak but positive fluorescence was observed in the pass 3 cultures up to time of harvest at 6 weeks after inoculation. Pass 4 cultures were positive at 3 weeks. By pass 5, fluorescence was positive at 1 week and most cells were stained at 2 weeks. Pass 6 cells were positive at 1 week. By 3 weeks, about 60% of the cells were stained. In 7th passage, greater than 90% of the cells were positive by 5 weeks.

Inoculation of cells with the stool extract containing HM-175 was repeated, and the cells were maintained for a longer period of time (Table 2). Intense granular fluorescence in occasional cells was observed after 1 week. The fluorescence then disappeared during weeks 2 and 3 but could be observed again after 4 weeks, when very few cells were positively stained but focal fluorescence was observed. At 8 weeks, intensely staining focal areas of rounded cells were observed. Positive fluorescence continued through the final observation at 12 weeks.

Two weeks after inoculation, whole cells harvested from the first AGMK cell passage of HM-175 stool (flasks) were used for pass 2 inoculations of cells in T-75 flasks. At eight weeks, cells scraped from these pass 2 flask cultures were strongly positive for antigen and almost all cells were stained. The RIA (P/N) value of the cell extract was 14.3. The RIA of the supernatant was negative. Pass 2 cells were used for pass 3. Almost 100% of the pass 3 cells exhibited intense staining by four weeks postinoculation, and the RIA of the cell extract was 23.7. RIA of the supernatant was again negative. Two weeks after inoculation of the fourth passage, intense fluorescence was observed in approximately 10% of the cells. By 3 weeks, intense staining was observed in approximately 60% of the cells. At 5 weeks almost 100% of the cells were stained, and the RIA P/N was 22.4 on the extract of the cell pellet, but negative on the supernatant. Blocking experiments with hyperimmune chimpanzee serum at this passage level confirmed the specificity of the fluorescence: convalescent but not preinfection serum completely blocked the fluorescence. Pass 5 cultures were positive after 1 week, and by 3 weeks, 80–90% of the cells were intensely stained. Blocking experiments at this passage level were performed with paired humal pre-exposure and convalescent sera and pre-exposure and hyperimmune chimpanzee sera. Only the sera containing anti-HAV blocked the fluorescence. Pass 6 and 7 cells were also positive by 1 week and the number of positive cells increased with time.

The specificity of the tissue culture-derived HA Ag was further proven by RIA blocking experiments—when used as the source of antigen for a solid-phase RIA blocking test, the HA AG reactivity was blocked by convalescent sera from a chimpanzee and a marmoset experimentally infected with the HM-175 strain of HAV and by convalescent sera from three humans who were naturally infected with the SD-11 strain of HAV. None of the pre-infection sera blocked HA Ag reactivity, nor did pre- and convalescent-sera from one human and two chimpanzee cases of hepatitis B virus infection.

This invention shows that HAV can be isolated and serially propagated in AGMK cell culture taken directly from human specimens. The virus isolated from stool experienced an eclipse phase lasting approximately 4 weeks, after which the amount of HA Ag increased. The serial passage of HM-175 substantially decreases the interval to maximum intracellular HA Ag expression.

EXAMPLES

Primary isolation of HAV in AGMK cell culture was conducted according to the specifications of this application using three strains of HAV: MS-1, SD-11, and HM-175. The cells were stained by direct immunofluorescence (IF) to establish the identify of the virus. Fluorescein-labeled anti-HAV was applied to acetone-fixed cell culture coverslips. The amount of HA Ag was determined on a scale of 1 to 4, 4 indicating that the cell sheet contained almost 100% intensely staining cells. The results are shown below:

| Strain | Inoculum | IF by Week 1 | 1 | 3 |
|---|---|---|---|---|
| MS-1 | Stool | — | — | — |
| MS-1 | Serum | — | — | — |
| SD-11 | Stool | ± | — | ± |
| SD-11 | Serum | — | 1 | 2 |
| HM-175 | Stool | 1 | 1 | 3 |

For additional experiments, see Table 2.

We claim:

1. A method for the direct isolation of HAV strain HM-175 taken from stool samples of humans with acute hepatitis A virus, propagating the virus in a suitable substrate, and serially passaging said virus to form an agent for a vaccine without interposition of a mammalian model.

2. A method for the in vitro propagation of hepatitis A virus by cultivating HAV strain HM-175 in primary African Green Monkey kidney (AGMK) cell cultures, and serially passaging said virus at least 5 times in AGMK without the interposition of a mammalian model.

3. In the method for direct isolation of HAV taken from stool samples of humans with acute hepatitis A, and further isolating and propagating the virus in a suitable substrate, the step which comprises directly passaging said virus in tissue culture cells to form a serological test or radioimmunoassay of anti-HAV without interposition of a mammalian model.

* * * * *